US00PP34043P2

(12) United States Plant Patent
Kordes

(10) Patent No.: US PP34,043 P2
(45) Date of Patent: Mar. 22, 2022

(54) FLORIBUNDA ROSE PLANT NAMED 'KORHESANWES'

(50) Latin Name: *Rosa hybrida*
Varietal Denomination: KORhesanwes

(71) Applicant: W. KORDES' SÖHNE Rosenschulen GmbH & Co KG, Klein Offenseth-Sparrieshoop (DE)

(72) Inventor: Wilhelm Alexander Kordes, Klein Offenseth-Sparrieshoop (DE)

(73) Assignee: W. KORDES' SÖHNE Rosenschulen GmbH & Co KG, Klein Offenseth-Sparrieshoop (DE)

( * ) Notice: Subject to any disclaimer, the term of this patent is extended or adjusted under 35 U.S.C. 154(b) by 0 days.

(21) Appl. No.: 17/314,593

(22) Filed: May 7, 2021

(51) Int. Cl.
*A01H 5/02* (2018.01)
*A01H 6/74* (2018.01)

(52) U.S. Cl.
USPC ..... Plt./145
CPC ..... *A01H 6/749* (2018.05)

(58) Field of Classification Search
USPC ..... Plt./145
CPC ..... A01H 6/749
See application file for complete search history.

(56) References Cited

U.S. PATENT DOCUMENTS

PP15,076 P2 8/2004 Carruth

OTHER PUBLICATIONS

2022 Rose Catalog' Star® 5 Roses and Plants, https://issuu.com/starrosesandplants/dcs/2022_rosecatalog?fr=sNmJkZjil4MzEzMjilpublished Mar. 3, 2021.*
"2022 Rose Catalog" Star® Roses and Plants published on Mar. 3, 2021.

* cited by examiner

*Primary Examiner* — Anne Marie Grunberg
(74) *Attorney, Agent, or Firm* — Panitch Schwarze Belisario & Nadel LLP; Stephany G. Small; Travis W. Bliss

(57) ABSTRACT

A new and distinct variety of floribunda rose plant, referred to by its cultivar name, 'KORhesanwes', is described. The new variety forms in abundance on a substantially continuous basis attractive, yellow colored blossoms suffused with orange. The vegetation is vigorous, and the growth habit is very bushy and upright. Attractive semi-glossy, medium green foliage is formed. Additionally, the new variety is particularly well suited for growing as distinctive ornamentation in the landscape.

1 Drawing Sheet

Latin name of genus and species of plant claimed: *Rosa hybrida.*

Variety denomination: 'KORhesanwes'.

BACKGROUND OF THE INVENTION

The new variety of floribunda rose plant of the present invention was created by controlled breeding in May 2008 in Sparrishoop, Germany by artificial pollination wherein two parents were crossed which previously had been studied in the hope that they would contribute the desired characteristics. The female parent (i.e., the seed parent) of the new variety was a seedling (non-patented) from a cross of 'INTERflocu' (non-patented) x unnamed seedling. The male parent (i.e., the pollen parent) of the new variety was 'NOA75800' (non-patented).

The parentage of the new variety can be summarized as follows:

('INTERflocu' x unnamed seedling) x 'NOA75800'

The seeds resulting from the above pollination were sown and small plants were obtained which were physically and biologically different from each other. Selective study resulted in the identification of a single plant of the new variety.

The new variety has been found to undergo asexual propagation at Wasco, Calif. and Cochranville, Pa. by a number of routes such as vegetative cuttings. Asexual propagation techniques in Wasco, Calif. and Cochranville, Pa., such as vegetative cuttings, have shown that the characteristics of the new variety are homogeneous, stable, and strictly transmissible by such asexual propagation from one generation to another. Accordingly, the new variety undergoes asexual propagation in a true-to-type manner.

SUMMARY OF THE INVENTION

It was found that the new variety of floribunda rose plant of the present invention possesses the following combination of characteristics:

(a) abundantly and substantially continuously forms attractive, yellow colored blossoms suffused with orange,
(b) exhibits a very bushy and upright growth habit,
(c) forms vigorous vegetation, and
(d) forms attractive ornamental semi-glossy, medium green foliage.

The new variety well meets the needs of the horticultural industry. It can be grown to advantage as attractive ornamentation in parks, gardens, public areas, and residential landscapes. Accordingly, it is particularly well suited for growing in the landscape.

The new variety can be readily distinguished from its ancestors. More specifically, the unnamed seedling seed parent originating from the ('INTERflocu' x unnamed seedling) cross displays a different flower shape and more petals per flower compared to the new variety. Additionally, the 'NOA75800' (i.e., the pollen parent) displays a smaller flower size compared to the new variety. Moreover, the new variety can be readily distinguished from non-parental related similar varieties. For example, 'WEKscemala' (U.S. Plant Pat. No. 15,076) displays more petals per flower and foliage that is darker green colored and more glossy compared to the new variety.

The new variety has been named the 'KORhesanwes' variety.

The first offer for sale of the new variety was in "2022 ROSE CATALOG" *Star® Roses and Plants*, which was published on Mar. 3, 2021 by the inventor or by another who obtained the new variety directly or indirectly from the inventor.

BRIEF DESCRIPTION OF THE PHOTOGRAPH

The accompanying photograph shows, as nearly true as it is reasonably possible to make the same in a color illustration of this character, a typical specimen of the new variety and blossoms of the new variety. The illustrated rose plant of the new variety was approximately two years of age and was grown outdoors in a three-gallon container on its own roots at Cochranville, Pa., U.S.A. in May 2020.

The drawing sheet illustrates a specimen of the plant displaying flowers at varying points of opening.

DETAILED BOTANICAL DESCRIPTION

The chart used in the identification of colors is that of The Royal Horticultural Society (R.H.S. Colour Chart, 2015 edition). The terminology which precedes reference to the chart has been added to indicate the corresponding color in more common terms. The description is based on a two-year-old specimen of the new variety, observed during March, while growing on its own roots in a greenhouse in a three-gallon container in Cochranville, Pa.

Botanical classification: *Rosa hybrida* cultivar KORhesanwes.

Plant:

*Height*.—Approximately up to 57.0 cm from the top of the soil plane.

*Width*.—Approximately up to 45.0 cm.

*Habit*.—Very bushy and upright.

Branches:

*Stem color*.—Old wood: commonly near Green Group 138A. — young stems: commonly near Green Group 143A.

*Length*.—Main stems: approximately 23.0 cm on average. — secondary stems: approximately 9.0 cm on average.

*Diameter*.—Main stems: approximately 7.0 mm on average. — secondary stems: approximately 3.0 mm on average.

*Thorns*.—Amount: moderate, 3 to 4 per internode. — young thorns: length is approximately 5.0 mm on average; width is approximately 3.0 mm at point of attachment; color is commonly near Red Group 37A. — old thorns: length is approximately 6.0 mm on average, width is approximately 3.0 mm at point of attachment; color is commonly near Greyed-Orange Group 177A.

Leaflets:

*Number*.—3, 5, and 7.

*Shape*.—Ovate; apex shape is acute to acuminate; and base shape is cuneate.

*Margin*.—Serrate.

*Undulation*.—Moderate.

*Texture*.—Upper surface: smooth. — under surface: smooth.

*Size*.—Terminal leaflet: length is approximately 6.0 cm on average; width is approximately 3.8 cm on average. — lower leaflets: length is approximately 4.0 cm on average; width is approximately 2.5 cm on average. — 5-Leaflet leaf: length is approximately 12.0 cm on average; width is approximately 9.0 cm on average.

Foliage:

*Young foliage*.—Upper surface color: commonly near Green Group 139A with indistinguishable venation. — under surface color: commonly near Green Group 137C with indistinguishable venation.

*Old foliage*.—Upper surface color: commonly near Green Group 137A with indistinguishable venation. — under surface color: commonly near Yellow-Green Group 147B with venation of near Greyed-Orange Group 172A.

*Petiole*.—Texture: upper surface is smooth; under surface is smooth. — length: approximately 3.0 cm on average. — diameter: approximately 1.0 mm on average. — upper surface color: commonly near Green Group 137A. — under surface color: commonly near Yellow-Green Group 144A.

*Rachis*.—Upper surface color: commonly near Green Group 137A. — under surface color: commonly near Yellow-Green Group 144A. — length: approximately 8.0 cm on average. — diameter: approximately 1.0 mm on average.

*Stipules*.—Length: approximately 1.5 cm on average. — width: approximately 5.0 mm on average. — margin: Entire to erose. — upper surface color: commonly near Green Group 143B. — lower surface color: commonly near Green Group 143C.

Inflorescence:

*Number of flowers*.—About 26 blooms on average on a plant at once.

*Number of blossoms per stem or in a cluster*.—Typically, between 2 and 4 blooms per stem on average.

*Blooming season*.—Typically, in bloom outdoors from May to November in Southeastern Pennsylvania.

*Peduncle*.—Color: commonly near Green Group 143A. — diameter: approximately 3.0 mm on average. — length: approximately 3.0 cm on average. — surface texture: smooth.

*Sepals*.—Number: 5. — upper surface color and texture: commonly near Green Group 143A, covered in short pubescence. — under surface color and texture: commonly near Yellow-Green Group 148B; puberulent. — size: length is approximately 1.5 cm on average; width is approximately 9.0 mm on average. — margin: entire with extension on two or three sepals measuring 5.0 mm in length and 1.0 mm in width. — apex: acute to aristate. — base: truncate as it joins the receptacle.

*Buds*.—Shape: ovoid. — size: length is approximately 1.5 cm on average; width is approximately 1.3 cm on average. — color (when opening): commonly near Yellow Group 9A.

*Flower*.—Form: double, cuplike. — profile: flat to slightly concave as it opens. — diameter: approximately 6.5 cm on average. — height: approximately 2.7 cm on average. — duration: on the plant approximately 10 days. — petal color when first and fully opened: upper surface is commonly near Yellow Group 6C; under surface is commonly near Yellow Group 7C. — petal color at end of blooming: upper surface is commonly near Yellow-Orange Group 19D with Red Group 37C around edge of petal; under surface is commonly near Yellow Group 4D.

*Petaloids*.—Color: commonly near Yellow Group 6C. — number: 5. — length: approximately 1.5 cm on average. — width: approximately 5.0 mm on average.

*Fragrance*.—Slight sweet scent.

*Petal*.—Number: 17 on average. — drop: good. — length: approximately 3.0 cm on average. — width: approximately 3.4 cm on average. — overall shape: broadly obovate. — margin: entire with moderate undulation. — apex shape: rounded to slightly cuspidate. — base shape: cuneate. — basal spot: absent. — petals reflex: one by one.

*Stamen*.—Number: approximately 120. — anthers: number is approximately 120; color is commonly near Yellow-Orange Group 20A; length is approximately 3.0 mm; shape is oval. — filaments: length is approximately 2.0 mm on average; color is commonly near Yellow Group 12A.

*Pistils*.—Arrangement: separate and free. — number: approximately 96. — style: length is approximately 4.0 mm; color is commonly near Red Group N45D. — stigma: diameter is approximately 1.0 mm; shape is fan shaped.

*Receptacle*.—Size: 8.0 mm diameter. — depth: 6.0 mm. — shape: urn shaped. — color: commonly near Green Group 143A. — surface texture: smooth.

*Pollen*.—Color: commonly near Yellow-Orange Group 20A. — amount: sparse.

*Hips/seed*.—None observed.

Development:

*Vegetation*.—Semi-glossy, medium green, vigorous and strong.

*Blossoming*.—Abundant and substantially continuous from spring through frost.

*Resistance to diseases*.—Very good resistance for powdery mildew (*Sphaerotheca pannosa*) and rust (*Phragmidium tuberculatum* and *Phragmidium mucronatum*).

*Hardiness*.—Hardy to USDA Zone 5.

The new 'KORhesanwes' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of floribunda rose plant named 'KORhesanwes' characterized by the following combination of characteristics:

(a) abundantly and substantially continuously forms attractive, yellow colored blossoms suffused with orange, (b) exhibits a very bushy and upright growth habit, (c) forms vigorous vegetation, and (d) forms attractive ornamental semi-glossy, medium green foliage;

substantially as herein shown and described.

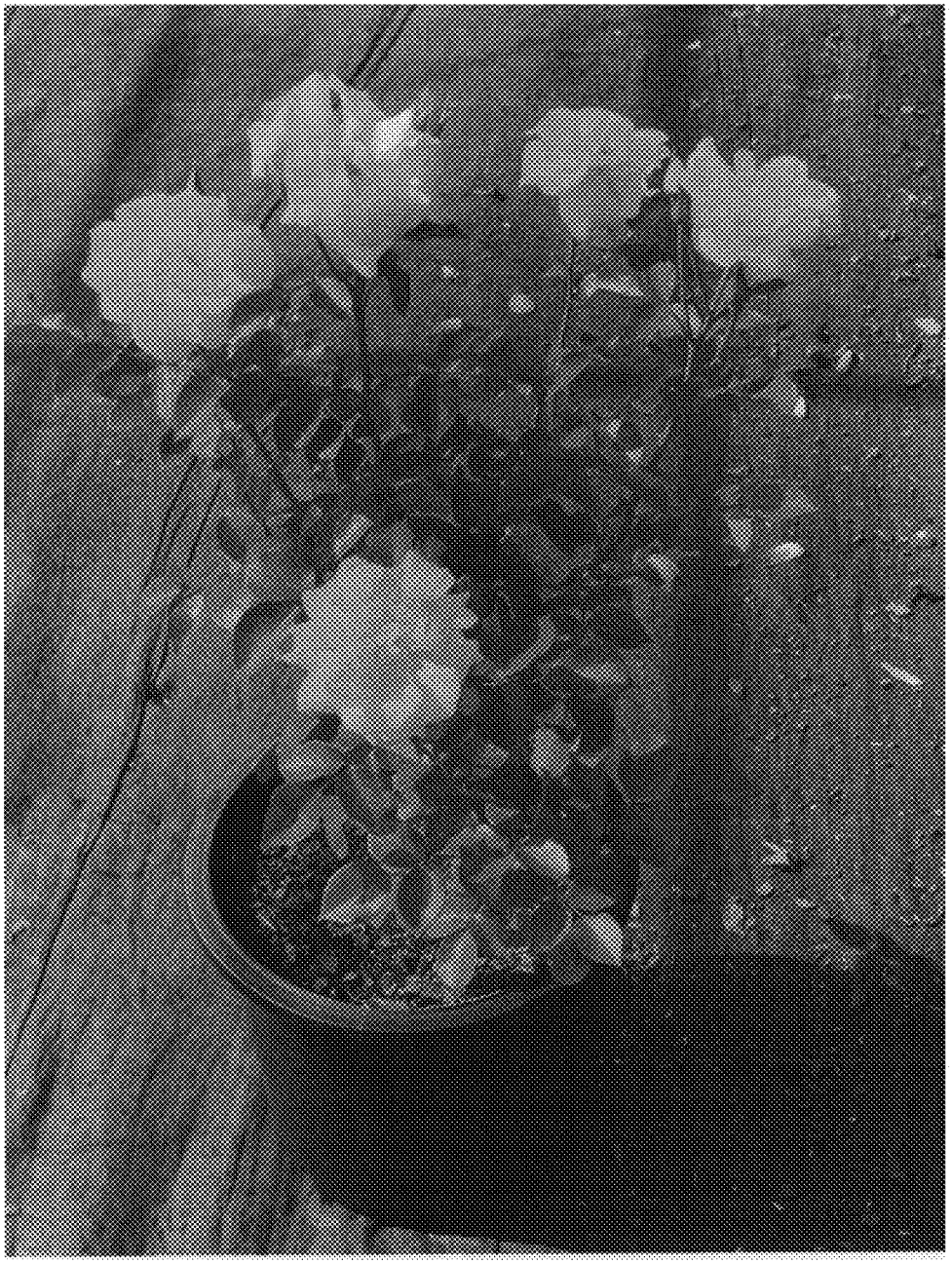

* * * * *